(12) United States Patent
Pan et al.

(10) Patent No.: US 11,935,279 B1
(45) Date of Patent: Mar. 19, 2024

(54) WEAKLY SUPERVISED PATHOLOGICAL IMAGE TISSUE SEGMENTATION METHOD BASED ON ONLINE NOISE SUPPRESSION STRATEGY

(71) Applicant: GUILIN UNIVERSITY OF ELECTRONIC TECHNOLOGY, Guangxi (CN)

(72) Inventors: Xipeng Pan, Guangxi (CN); Huahu Deng, Guangxi (CN); Rushi Lan, Guangxi (CN); Zhenbing Liu, Guangxi (CN); Lingqiao Li, Guangxi (CN); Huadeng Wang, Guangxi (CN); Xinjun Bian, Guangxi (CN); Yajun An, Guangxi (CN); Feihu Hou, Guangxi (CN)

(73) Assignee: Guilin University of Electronic Technology, Guangxi (CN)

( * ) Notice: Subject to any disclaimer, the term of this patent is extended or adjusted under 35 U.S.C. 154(b) by 0 days.

(21) Appl. No.: 18/505,639

(22) Filed: Nov. 9, 2023

(30) Foreign Application Priority Data

Dec. 20, 2022 (CN) .......................... 202211643031.X

(51) Int. Cl.
*G06V 10/778* (2022.01)
*G06T 7/11* (2017.01)
(Continued)

(52) U.S. Cl.
CPC .............. *G06V 10/778* (2022.01); *G06T 7/11* (2017.01); *G06T 7/136* (2017.01); *G06T 7/194* (2017.01);
(Continued)

(58) Field of Classification Search
CPC .. G06V 10/778; G06V 10/764; G06V 10/776; G06V 10/86; G06V 20/50;
(Continued)

(56) References Cited

U.S. PATENT DOCUMENTS

| 10,453,200 | B2 * | 10/2019 | Mukherjee | ............ | G06N 3/045 |
| 11,302,444 | B2 * | 4/2022 | Chen | ...................... | G16H 50/20 |

(Continued)

FOREIGN PATENT DOCUMENTS

| CN | 113674288 A | 11/2021 |
| CN | 114565605 A | 5/2022 |

(Continued)

OTHER PUBLICATIONS

Chu Han et al., "Multi-Layer Pseudo-Supervision for Histopathology Tissue Semantic Segmentation using Patch-level Classification Labels," Medical Image Analysis, Aug. 2022.

(Continued)

*Primary Examiner* — Bobbak Safaipour
(74) *Attorney, Agent, or Firm* — Pilloff Passino & Cosenza LLP; Sean A. Passino; Rachel K. Pilloff

(57) ABSTRACT

Provided is a weakly supervised pathological image tissue segmentation method based on an online noise suppression strategy, including: acquiring a hematoxylin-eosin (H&E) stained graph, processing the H&E stained graph to obtain a data set, dividing the data set, training a classification network based on a divided data set, and generating a pseudo-label; suppressing a noise existing in the pseudo-label based on the online noise suppression strategy, and training a semantic segmentation network through the pseudo-label after noise suppression and a training set corresponding to the pseudo-label to obtain a prediction result of the semantic segmentation network after the training, and taking the prediction result as a final segmentation result.

7 Claims, 5 Drawing Sheets

(51) Int. Cl.
   *G06T 7/136*       (2017.01)
   *G06T 7/194*       (2017.01)
   *G06V 10/764*      (2022.01)
   *G06V 10/776*      (2022.01)
   *G06V 10/86*       (2022.01)
   *G06V 20/50*       (2022.01)
   *G06V 20/70*       (2022.01)
   *G16H 30/40*       (2018.01)
   *G16H 70/60*       (2018.01)

(52) U.S. Cl.
   CPC .......... *G06V 10/764* (2022.01); *G06V 10/776* (2022.01); *G06V 10/86* (2022.01); *G06V 20/50* (2022.01); *G06V 20/70* (2022.01); *G16H 30/40* (2018.01); *G16H 70/60* (2018.01); *G06T 2207/20021* (2013.01); *G06T 2207/20081* (2013.01); *G06T 2207/20084* (2013.01); *G06T 2207/30024* (2013.01); *G06T 2207/30061* (2013.01); *G06T 2207/30068* (2013.01); *G06T 2207/30096* (2013.01); *G06V 2201/03* (2022.01)

(58) Field of Classification Search
   CPC ...... G06V 20/70; G06V 2201/03; G06T 7/11; G06T 7/136; G06T 7/194; G06T 2207/20021; G06T 2207/20081; G06T 2207/20084; G06T 2207/30024; G06T 2207/30061; G06T 2207/30068; G06T 2207/30096; G16H 30/40; G16H 70/60
   See application file for complete search history.

(56) References Cited

U.S. PATENT DOCUMENTS

| | | | |
|---|---|---|---|
| 11,376,441 B2* | 7/2022 | Chennubhotla | G16H 30/40 |
| 2014/0233826 A1* | 8/2014 | Agaian | G16H 50/20 |
| | | | 382/133 |
| 2019/0258855 A1* | 8/2019 | Madabhushi | G06F 18/2415 |
| 2022/0036971 A1* | 2/2022 | Yoo | G06V 20/698 |
| 2023/0357698 A1* | 11/2023 | Austerjost | G06V 20/698 |
| 2023/0419694 A1* | 12/2023 | Stumpe | G06T 7/0012 |
| 2023/0420072 A1* | 12/2023 | Yoo | G06N 3/02 |

FOREIGN PATENT DOCUMENTS

| | | |
|---|---|---|
| CN | 114821052 A | 7/2022 |
| CN | 114937045 A | 8/2022 |
| EP | 3611654 A1 | 2/2020 |
| WO | 2021184817 A1 | 9/2021 |
| WO | 2022100034 A1 | 5/2022 |

OTHER PUBLICATIONS

Notice of the First Office Action for China Application No. 202211643031.X, dated Jul. 13, 2023.

Notification to Grant Patent Right for China Application No. 202211643031.X, dated Aug. 14, 2023.

First Search Report for China Application No. 202211643031.X.

Supplementary Search Report for China Application No. 202211643031.X.

* cited by examiner

WEAKLY SUPERVISED PATHOLOGICAL IMAGE TISSUE SEGMENTATION METHOD BASED ON ONLINE NOISE SUPPRESSION STRATEGY

CROSS-REFERENCE TO RELATED APPLICATIONS

This application claims priority to Chinese Patent Application No. 202211643031.X, filed on Dec. 20, 2022, the contents of which are hereby incorporated by reference.

TECHNICAL FIELD

The disclosure relates to the technical field of digital pathology and deep learning, and in particular to a weakly supervised pathological image tissue segmentation method based on an online noise suppression strategy.

BACKGROUND

Tumor microenvironment (TME) is a complex environment in which tumor cells live, and the TME plays an important role in development, metastasis and prognosis of tumors. At a tissue level, the TME includes tumor epithelium, tumor-associated stroma and tumor-infiltrating lymphocytes (TILs), etc. An interaction between the tumor epithelium and the tumor-associated stroma is related to the development of the tumors. Densities and spatial distribution of the TILs have been proved to be biomarkers for prognosis of many tumors, such as lung cancer, breast cancer and colorectal cancer. Therefore, tissue segmentation is very important for accurate quantification of the TME.

In recent years, with development of digital scanner technology, a large number of pathological slides generate Whole Slide Images (WSIs), which provides sufficient "fuel" for pathological image analysis based on artificial intelligence. However, most existing methods need intensive pixel-level labels for training, and it is very expensive and time-consuming to obtain such pixel-level labels for pathological images. Because of diversity and complexity of the pathological images, only professional pathologists or doctors with clinical background may label the pathological images.

At present, artificial intelligence technology, especially deep learning technology, has achieved a lot in the field of biomedical image processing. Only using patch-level labels to segment the pathological images may greatly reduce a time-consuming and laborious pixel-level labeling cost. Pathologists only need to judge whether there is a certain tissue category in a patch, and do not need to draw a boundary of the tissue carefully on a pathological image, thus greatly reducing a workload of data labeling.

SUMMARY

An objective of the disclosure is to provide a weakly supervised pathological image tissue segmentation method based on an online noise suppression strategy. By using a classification algorithm and a segmentation algorithm of digital pathology and deep learning, tissue segmentation of hematoxylin-eosin staining (H&E) stained images of lung cancer/breast cancer may be realized only by using patch-level labels, and a pixel-level segmentation result may be generated, so that spatial distribution of a internal tissue structure of a tumor may be intuitively displayed.

In order to achieve the above objective, the disclosure provides a following scheme:

A weakly supervised pathological image tissue segmentation method based on an online noise suppression strategy including:
    acquiring a hematoxylin-eosin (H&E) stained graph, processing the H&E stained graph to obtain a data set, dividing the data set, training a classification network based on a divided data set, and generating a pseudo-label;
    suppressing a noise existing in the pseudo-label based on the online noise suppression strategy, and training a semantic segmentation network through the pseudo-label after noise suppression and a training set corresponding to the pseudo-label to obtain a prediction result of the semantic segmentation network after the training, and taking the prediction result as a final segmentation result.

Optionally, acquiring the H&E stained graph includes:
    collecting pathological section images of cancerous tissues of lung cancer/breast cancer patients, dyeing the pathological section images to obtain H&E stained pathological sections of lung cancer/breast cancer, and then digitizing the H&E stained pathological sections of the lung cancer/breast cancer to obtain the H&E stained graph.

Optionally, processing the H&E stained graph includes:
    delineating a region of interest of the H&E stained graph, cutting the region of interest into sub-image blocks of a same series without overlapping, adding a patch-level label to each of the sub-image blocks, and specifying a tissue category existing in the patch-level label.

Optionally, dividing the data set, training the classification network based on the divided data set, and generating the pseudo-label include:
    dividing the training set, a verification set and a test set according to the data set, constructing the classification network by using a deep learning model, carrying out data enhancement processing on the training set, training the classification network based on the training set after the data enhancement processing, internally verifying classification performance of the classification network through the verification set, and externally verifying the classification performance of the classification network through the test set to obtain a trained classification network, and using Grad-CAM++ to generate the pseudo-label based on the trained classification network.

Optionally, training the classification network based on the training set after the data enhancement processing includes:
    pre-training the classification network based on a large public image database to obtain an initial model of the classification network, setting a training scheme and hyper parameters of the initial model of the classification network, training the initial model of the classification network based on the training set after the data enhancement processing, introducing a progressive attention-discarding mechanism, and iteratively erasing most discriminating regions, forcing the initial model of the classification network to learn non-discriminating regions;
    where a weight of each layer of the initial model of the classification network is set to an updatable mode.

Optionally, suppressing the noise existing in the pseudo-label based on the online noise suppression strategy includes:

calculating the pseudo-label and prediction confidence pixel by pixel based on standard cross entropy to obtain a loss map, selecting a loss of the loss map by improving a weighted cross entropy loss, and giving different weights to different pixel points according to the loss of the loss map to suppress the noise existing in the pseudo-label.

Optionally, a method for improving the weighted cross entropy loss includes is:

$$\mathcal{L}_{seg} = -\sum_{j=0}^{w}\sum_{i=0}^{h} W_{i,j} \cdot \log \frac{\exp(P_{\mathcal{M}_{i,j},i,j})}{\sum_{c=1}^{C}(\exp(P_{c,i,j}))}$$

wherein $\mathcal{L}_{seg}$ is a loss of a segmentation network, $W \in \mathbb{R}^{H+W}$ is a loss weight, H and W respectively represent dimensions, and i and j respectively represent coordinates, P is prediction of the segmentation network, $\mathcal{M}$ is the pseudo-label, and C is a category.

Optionally, a method of giving different weights to the different pixel points is:

$$W = \frac{sm(-\mathcal{L})}{\text{mean}(sm(-\mathcal{L}))}$$

where $sm(-\mathcal{L})$ is to assign a high loss value to a low value, sm is to use a softmax function in HW dimensions, and mean($sm(-\mathcal{L})$) is an average value of assigning the high loss value to the low value, sm is the softmax function, and a loss in $\mathcal{L} \in \mathbb{R}^{H+W}$ is used as an index indicating a degree of learning difficulty, and W is a weight.

Optionally, training the semantic segmentation network through the pseudo-label after the noise suppression and the training set corresponding to the pseudo-label include:
carrying out the data enhancement processing on the training set corresponding to the pseudo-label, setting the training scheme and the hyper parameters of the classification network, and training the semantic segmentation network through the pseudo-label after the noise suppression and the training set after the data enhancement processing.

Optionally, taking the prediction result of the semantic segmentation network after the training as the final segmentation result includes:
using an overlapping sliding window prediction operation under a preset magnification of the H&E stained graph, intercepting image blocks with a same pixel size, and obtaining a overlapping rate of the image blocks, sending the image blocks into the semantic segmentation network after the training to obtain probability maps of several channels, stitching the probability maps into a whole slide image (WSI) level, calculating an average value of each category prediction probability of each pixel position for overlapping regions, and acquiring a WSI segmentation result through an argmax operation;
segmenting the probability maps stitched as the WSI level by a threshold segmentation method when a background region is segmented, and setting points with gray scale pixel values greater than a preset value as fixed values to obtain a gray scale map; and
adding the gray scale map to the WSI segmentation result to obtain the final segmentation result.

The disclosure has beneficial effects as follows.

The disclosure provides the weakly supervised pathological image tissue segmentation method based on the online noise suppression strategy, which uses a deep learning method to build a model to help segment a tissue in a pathological image and visually display the tissue. In principle, any number of tissue categories may be segmented to help a doctor analyze spatial heterogeneity of different tissue structures in tumors, thus contributing to prognosis analysis of lung cancer/breast cancer patients and formulating more appropriate treatment plans, which has great clinical significance.

BRIEF DESCRIPTION OF THE DRAWINGS

In the following, technical schemes in embodiments of the disclosure may be clearly and completely described with reference to attached drawings. Obviously, the described embodiments are only a part of the embodiments of the disclosure, but not all embodiments. Based on the embodiments in the disclosure, all other embodiments obtained by ordinary technicians in the field without a creative labor belong to a scope of protection of the disclosure.

DETAILED DESCRIPTION OF THE EMBODIMENTS

In the following, the technical scheme in the embodiment of the disclosure will be clearly and completely described with reference to the attached drawings. Obviously, the described embodiment is only a part of the embodiment of the disclosure, but not the whole embodiment. Based on the embodiments in the disclosure, all other embodiments obtained by ordinary technicians in the field without creative labor belong to the scope of protection of the disclosure.

Figure 1:
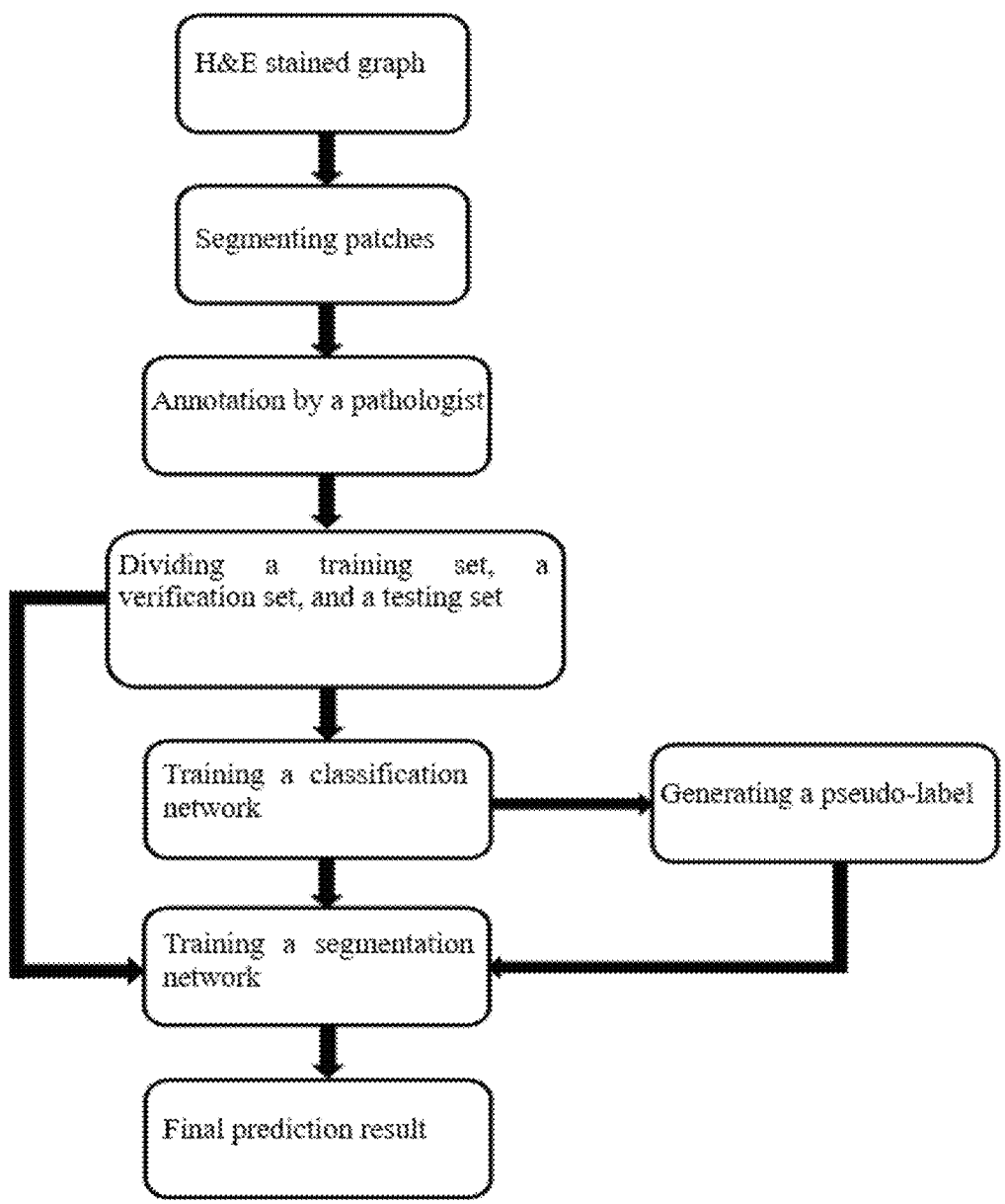
FIG. 1 is a flowchart of a weakly supervised pathological image tissue segmentation method based on an online noise suppression strategy according to an embodiment of the disclosure.

As shown in FIG. 1, a weakly supervised pathological image tissue segmentation method based on an online noise suppression strategy includes:
acquiring a hematoxylin-eosin (H&E) stained graph, processing the H&E stained graph to obtain a data set, dividing the data set, training a classification network based on a divided data set, and generating a pseudo-label;
suppressing a noise existing in the pseudo-label based on the online noise suppression strategy, and training a semantic segmentation network through the pseudo-label after noise suppression and a training set corresponding to the pseudo-label to obtain a prediction result of the semantic segmentation network after the training, and taking the prediction result as a final segmentation result.

In an embodiment, acquiring the H&E stained graph includes:
collecting pathological section images of cancerous tissues of lung cancer/breast cancer patients, dyeing the pathological section images to obtain H&E stained pathological sections of lung cancer/breast cancer, and then digitizing the H&E stained pathological sections of the lung cancer/breast cancer to obtain the H&E stained graph.

In an embodiment, processing the H&E stained graph includes:
delineating a region of interest of the H&E stained graph, cutting the region of interest into sub-image blocks of a same series without overlapping, adding a patch-level label to each of the sub-image blocks, and specifying a tissue category existing in the patch-level label.

In an embodiment, dividing the data set, training the classification network based on the divided data set, and generating the pseudo-label includes:
dividing the training set, a verification set and a test set according to the data set, constructing the classification network by using a deep learning model, carrying out data enhancement processing on the training set, training the classification network based on the training set after the data enhancement processing, internally verifying classification performance of the classification network through the verification set, and externally verifying the classification performance of the classification network through the test set to obtain a trained classification network, and using Grad-CAM++ to generate the pseudo-label based on the trained classification network.

In an embodiment, training the classification network based on the training set after the data enhancement processing includes:
pre-training the classification network based on a large public image database to obtain an initial model of the classification network, setting a training scheme and hyper parameters of the initial model of the classification network, training the initial model of the classification network based on the training set after the data enhancement processing, introducing a progressive attention-discarding mechanism, and iteratively erasing most discriminating regions, forcing the initial model of the classification network to learn non-discriminating regions;
where a weight of each layer of the initial model of the classification network is set to an updatable mode.

In an embodiment, suppressing the noise existing in the pseudo-label based on the online noise suppression strategy includes:
calculating the pseudo-label and prediction confidence pixel by pixel based on standard cross entropy to obtain a loss map, selecting a loss of the loss map by improving a weighted cross entropy loss, and giving different weights to different pixel points according to the loss of the loss map to suppress the noise existing in the pseudo-label In an embodiment, a method for improving the weighted cross entropy loss includes is:

$$\mathcal{L}_{seg} = -\sum_{j=0}^{w}\sum_{i=0}^{h} W_{i,j} \cdot \log \frac{\exp(P_{\mathcal{M}_{i,j},i,j})}{\sum_{c=1}^{C}(\exp(P_{c,i,j}))}$$

wherein $\mathcal{L}_{seg}$ is a loss of a segmentation network, $W \in \mathbb{R}^{H*W}$ is a loss weight, H and W respectively represent dimensions, and i and j respectively represent coordinates, P is prediction of the segmentation network, $\mathcal{M}$ is the pseudo-label, and C is a category.

In an embodiment, a method of giving different weights to the different pixel points is:

$$W = \frac{sm(-\mathcal{L})}{\text{mean}(sm(-\mathcal{L}))}$$

where $sm(-\mathcal{L})$ is to assign a high loss value to a low value, sm is to use a softmax function in HW dimensions, and mean($sm(-\mathcal{L})$) is an average value of assigning the high loss value to the low value, sm is the softmax function, and a loss in $\mathcal{L} \in \mathbb{R}^{H+W}$ is used as an index indicating a degree of learning difficulty, and W is a weight.

In an embodiment, training the semantic segmentation network through the pseudo-label after the noise suppression and the training set corresponding to the pseudo-label includes:
carrying out the data enhancement processing on the training set corresponding to the pseudo-label, setting the training scheme and the hyper parameters of the classification network, and training the semantic segmentation network through the pseudo-label after the noise suppression and the training set after the data enhancement processing.

In an embodiment, taking the prediction result of the semantic segmentation network after the training as the final segmentation result includes:
using an overlapping sliding window prediction operation under a preset magnification of the H&E stained graph, intercepting image blocks with a same pixel size, and obtaining a overlapping rate of the image blocks, sending the image blocks into the semantic segmentation network after the training to obtain probability maps of several channels, stitching the probability maps into a whole slide image (WSI) level, calculating an average value of each category prediction probability of each pixel position for overlapping regions, and acquiring a WSI segmentation result through an argmax operation;
segmenting the probability maps stitched as the WSI level by a threshold segmentation method when a background region is segmented, and setting points with gray scale pixel values greater than a preset value as fixed values to obtain a gray scale map of a background; and
adding the gray scale map to the WSI segmentation result to obtain the final segmentation result.

In order to make above objects, features and advantages of the disclosure more obvious and easy to understand, the disclosure will be further described in detail with attached drawings and specific embodiments.

This embodiment is a weakly supervised pathological image tissue segmentation method based on an online noise suppression strategy, including following steps:
collecting pathological section images of cancerous tissues of lung cancer/breast cancer patients, dyeing to obtain H&E stained pathological sections of lung cancer/breast cancer, and then digitizing the H&E stained pathological sections of the lung cancer/breast cancer to obtain an H&E stained graph. A dyeing treatment adopted in this embodiment is to use hematoxylin dye solution to dye chromatin in a nucleus and nucleic acid in the cytoplasm purple blue, and use eosin dye solution to dye components in the cytoplasm and extracellular matrix red.

Figure 2:
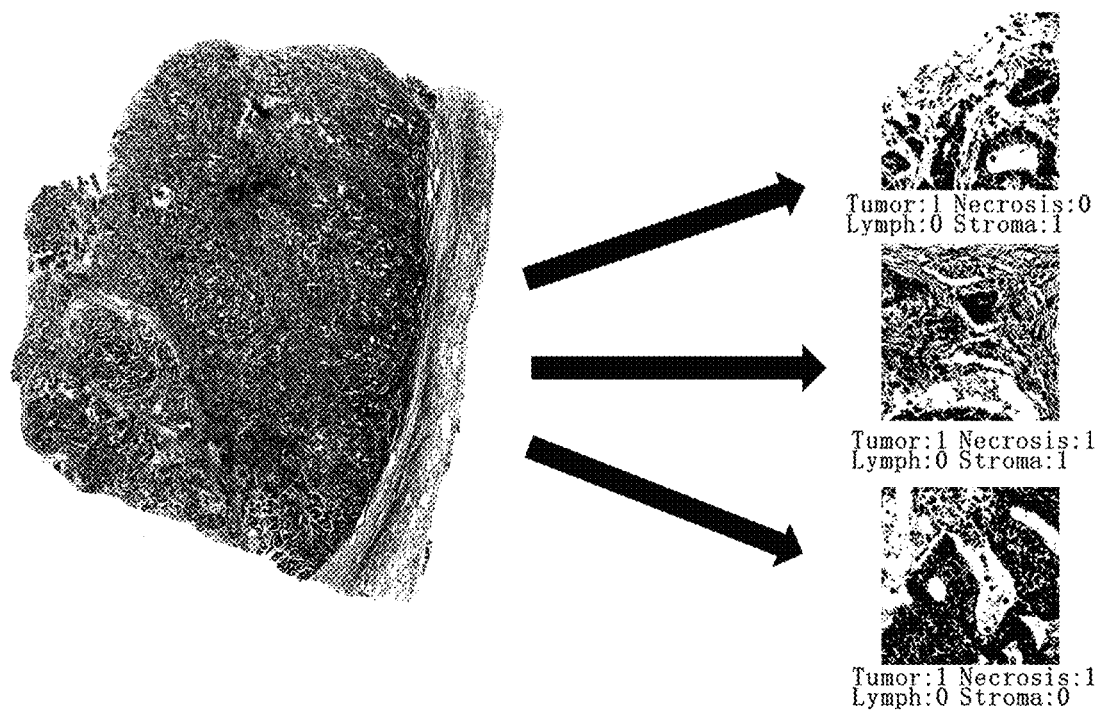
FIG. 2 is a schematic diagram of lung cancer hematoxylin-eosin (H&E) stained graph cut into image blocks and labeled according to an embodiment of the disclosure.

As shown in FIG. 2, a region of interest is delineated in the H&E stained graph, and the region of interest is divided into patches with a size of 224*224, and the patches are labeled by a pathologist in a form of one-hot coding. A doctor only needs to specify which tissue categories exist in a certain patch, where a pathological image of lung cancer includes four tissue categories: tumor epithelium (TE), tumor-associated stroma (TAS), necrosis (NEC), and lymphocytes (LYM). There are four tissue categories in a pathological image of breast cancer: tumor (TUM), stroma (STR), lymphatic infiltration (LYM) and necrosis (NEC).

Among them, the region of interest includes different tissue categories to obtain a data set. Specifically, the region of interest is divided into a series of sub-image blocks without overlapping, and according to a division result, a patch-level label is added to each of the sub-image blocks to indicate which tissue categories exist in a certain patch, so as to obtain a data set. In a lung adenocarcinoma data set, the label includes tumor epithelium (TE), tumor-associated stroma (TAS), necrosis (NEC), and lymphocytes (LYM), and a size of the sub-image blocks is set as a corresponding pixel at a magnification of 10×. In a breast cancer data set, the label includes tumor (TUM), stroma (STR), lymphatic infiltration (LYM) and necrosis (NEC), and a size of the sub-image blocks is set as a corresponding pixel at a magnification of 40×.

The training set of lung adenocarcinoma comes from 29 H&E stained WSIs, and the verification set and the test set come from 25 H&E stained WSIs, and data distribution after patch segmentation is as follows: a training set (16,678 patches with patch-level labels), a verification set (300 patches with pixel-level labels) and a test set (307 patches with pixel-level labels). The data set of breast cancer comes from 151 H&E stained WSIs, and the data division after patch segmentation is as follows: a training set is 23,422 patches (patch labeling), and a verification set and a test set are 3,418 and 4,986 patches (pixel-level labeling) respectively. The verification sets of the two data are used for internal verification of performance of a deep neural network, and the test sets are used for external verification of the performance of the deep learning network.

According to the data sets, a training set, a verification set and a test set are divided. A classification network is trained by using the training set of a patch-level label, and data enhancement processing is carried out on the training set. The verification set is used to verify classification performance of a neural network classifier internally. After a trained classification network is obtained, Grad-CAM++ is used to generate the pseudo-label of the training set.

In a classification stage, training the convolutional neural network classifier using the patch-level label training set includes: constructing a convolutional neural network classifier using a deep learning model in a field of machine learning technology, using a convolutional neural network ResNet38 pre-trained on a large public image database ILSVRC2012 as an initial model, setting a training scheme and hyper parameters, and then training the initial model using the training set, where a weight of each layer of the convolutional neural network is set to be updatable during the training. In order to generate a more accurate pseudo-label, and alleviate a region shrinkage problem existing in traditional CAM, that is, with an iteration of convolutional network training times, the classifier tends to focus on most discriminating regions of a target object. In this embodiment, the progressive attention-discarding mechanism is introduced to iteratively "erase" those most discriminating regions, thus forcing the classification network to learn other regions that are nondeterministic but belong to the object. In addition, the classification network is trained by a multi-label soft edge loss, and finally, on a trained classification network model, Grad-CAM++ is used to generate the pseudo-label, specifically as follows.

According to an obtained data set, a training set, a verification set and a test set are segmented, where in the classification stage, the training set is used for training the convolutional neural network classifier, the verification set is used for internally verifying classification performance of the convolutional neural network classifier, the test set is used for further externally testing the classification performance of the convolutional neural network classifier, and in a segmentation stage, the semantic segmentation network is trained by using the training set of the previous stage and a generated pseudo-label, the verification set is used for internally verifying performance of the semantic segmentation network, and the test set is used for further externally testing the performance of the semantic segmentation network.

In order to enhance the data and improve generalization of the network, in the classification stage, each image block in the obtained training set is randomly horizontally and flipped with a probability of 0.5. In the segmentation stage, random flipping, clipping and deformation data enhancement methods are used, and in a reasoning stage, multi-scale tests are used, including [0.75, 1, 1.25, 1.75, 2, 2.5, 3].

In the classification stage, the convolutional neural network classifier is constructed by using the deep learning model in the field of machine learning technology, and the convolutional neural network ResNet38, which has been pre-trained on the large public image database ILSVRC2012, is used as the initial model, and settings of the selected training scheme and the hyper parameters are specified as:
  1) using a stochastic gradient descent (SGD) algorithm as an optimization function when updating model parameters;
  2) using mini-batch gradient descent MBGD as the training scheme;
  3) setting a size of a hyper parameter mini-batch (batch-size) to 16;
  4) setting a size of epoch to 20;
  5) setting a learning rate to 0.01;
  6) using a multi-label soft edge loss function; and
  then training the initial model by using the training set, and setting a weight of each layer of the convolutional neural network to be updatable during training.

Figure 3:
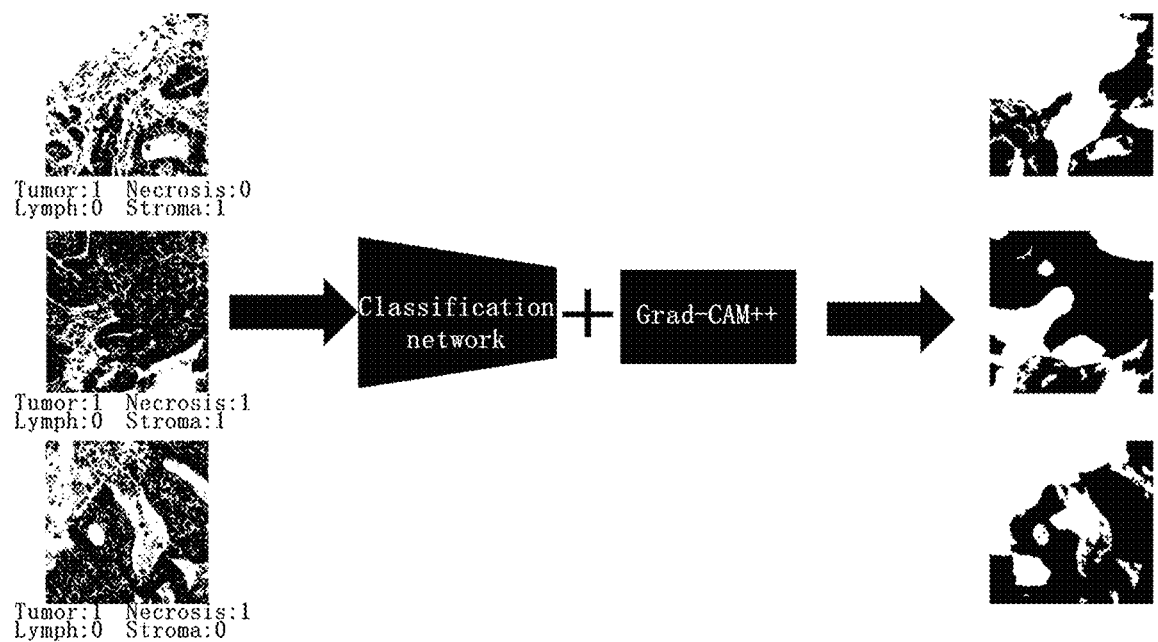
FIG. 3 is a schematic diagram of a process of generating a pseudo-label by a classification network according to an embodiment of the disclosure.

In order to generate the more accurate pseudo-label, and alleviate the region shrinkage problem existing in the traditional CAM, that is, with the iteration of convolutional network training times, the classifier tends to focus on the most discriminating regions of the target object. In this embodiment, the progressive attention-discarding mechanism is introduced to iteratively "erase" those most discriminating regions, thus forcing the classification network to learn other regions that are nondeterministic but belong to the object (that is, whether the classification network judges the discriminating regions or nondeterministic regions according to the focused regions of the object). Finally, on the trained classification network model, Grad-CAM++ is used to generate the pseudo-label, as shown in FIG. 3.

Training the semantic segmentation network by using the pseudo-label generated by the classification network and a corresponding training set, using the online noise suppression strategy to suppress an influence of noise existing in the pseudo-label on a segmentation model, thereby improving a segmentation accuracy. In a training process, the performance of the semantic segmentation network is internally verified by using the verification set, and then the performance of the semantic segmentation network is finally verified on the test set, and the prediction result of the semantic segmentation network is taken as a final segmentation result.

In the segmentation stage, this embodiment uses the training set and the pseudo-label generated by the classification network to train the semantic segmentation network. In this embodiment, PSPNet whose backbone is ResNet38 is used, and an SGD optimizer is used. The data enhancement includes random flipping, random clipping and deformation. Because the pseudo-label generated by the classification network inevitably has a noise, in order to alleviate an influence of this noise on the segmentation model, this embodiment proposes the online noise suppression strategy, specifically as follows.

Figure 4:
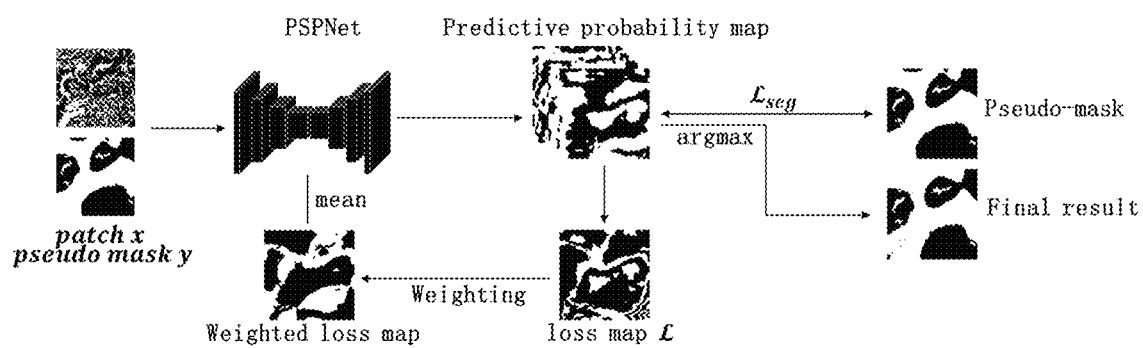
FIG. 4 is a schematic diagram of a tissue segmentation process of a segmentation network according to an embodiment of the disclosure.

As shown in FIG. 4, in the segmentation stage, in this embodiment, the training set and the pseudo-label generated by the classification network are used to train the semantic segmentation network. In this embodiment, PSPNet with the backbone of ResNet38 is adopted, and the settings of the selected training scheme and the hyper parameters are specified as:

1) using an SGD algorithm as an optimization function when updating model parameters;
2) using mini-batch gradient descent MBGD as the training scheme;
3) setting a size of a hyper parameter mini-batch (batch-size) to 16;
4) setting a number of iterations to 10000;
5) setting a learning rate to 5e-3; and
6) using an improved cross entropy loss function.

In this embodiment, prediction of the segmentation network may be P, and its pseudo-label is M. In this embodiment, the weighted cross entropy loss is improved, and may be expressed as:

$$\mathcal{L}_{seg} = -\sum_{j=0}^{w}\sum_{i=0}^{h} W_{i,j} \cdot \log \frac{\exp(P_{M_{i,j},i,j})}{\sum_{c=1}^{C}(\exp(P_{c,i,j}))}$$

where $\mathcal{L}_{seg}$ represents a loss of the segmentation network, $W \in \mathbb{R}^{H+W}$ represents a loss weight, i and j respectively represent coordinates, and H and W respectively represent a dimension and a weight, and C is used to represent a category. In order to obtain the loss weight, a loss on a loss map $\mathcal{L} \in \mathbb{R}^{H+W}$ is selected as an index to indicate a degree of learning difficulty, in which the loss map is calculated pixel by pixel through a standard cross entropy. This loss map is calculated based on the pseudo-label and prediction confidence, and includes rich information. Based on this index, in this embodiment, a strategy to suppress noise samples by using a loss map is proposed.

This strategy is based on a following observation: when a network predicts a noise pixel, if the confidence is high, a loss value of this pixel point will be high. On the contrary, those pixels supervised by more accurate signals have lower loss values. In order to suppress the noise pixel, in this embodiment, different weights are given to different pixel points according to the loss on the loss map. In other words, a purpose of this strategy is to give low weights to noise pixels and higher weights to accurate pixels. Specifically, in this embodiment, a negative sign is added to the loss map, and a softmax function sm is used in HW dimensions, and then divides it by its average value.

$$W = \frac{sm(-\mathcal{L})}{\text{mean}(sm(-\mathcal{L}))}$$

where sm(−L) is to give a low value to a high loss value and a high value to a low loss value, and finally each position is divided by the average value, so as to achieve a purpose of giving different weights according to the loss values.

A prediction result of a final model is obtained by using an argmax function.

Figure 5:
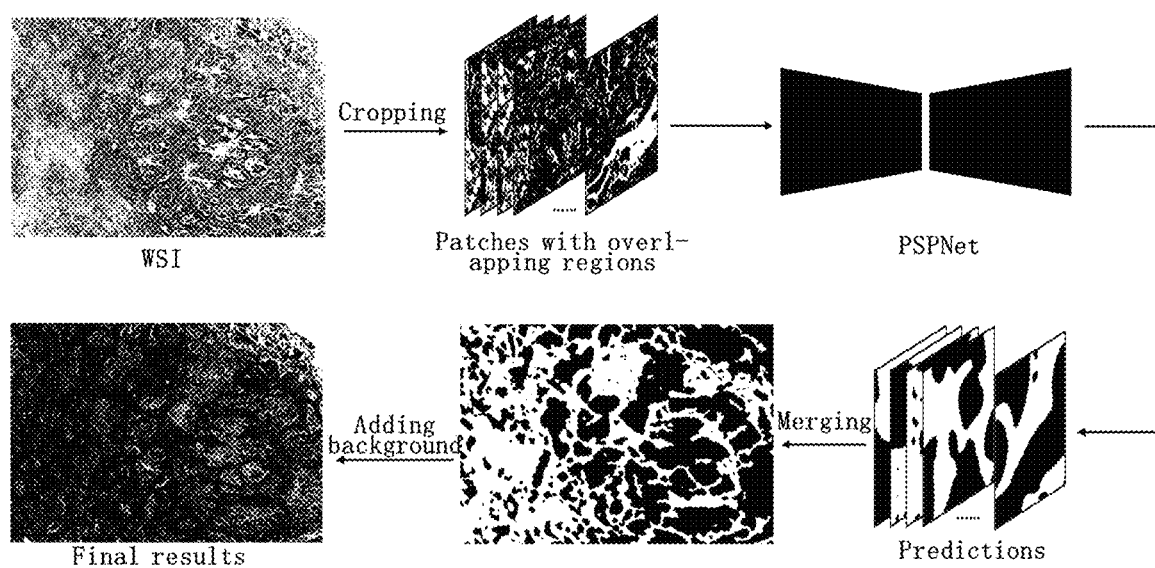
FIG. 5 is a schematic diagram of an entire whole slide image (WSI) segmentation process according to an embodiment of the disclosure.

As shown in FIG. 5, specific steps of tissue segmentation of the entire WSIs are as follows:

1) using an overlapping sliding window prediction operation under a magnification of 10× in the H&E stained graph of lung cancer, and intercepting a square image block with a size of 224*224 pixels at a time, with an overlapping rate of 50%, and sending the image block to a trained semantic segmentation network, and obtaining a probability map with a number of channels of n for each patch, corresponding to each category, and then stitching the probability map of each patch to a WSI level in this embodiment; for overlapping regions, calculating an average value of each category prediction probability of each pixel position, and finally, acquiring a WSI segmentation result by an argmax operation; and 2) when segmenting a background region (i.e. an unorganized region or a region that does not belong to the object), segmenting an original WSI image by using a threshold segmentation method, and setting a point with a gray scale pixel value greater than 210 as 255, otherwise remaining unchanged, and a specific operation is as follows:

ret, binary=cv2.threshold (gray, 210, 255, cv2.THRESH_BINARY); and after a gray scale map of the background is obtained, adding the gray scale map to a segmentation mask to get a final segmentation result.

According to the disclosure, classification algorithms of digital pathology and deep learning may be used to automatically identify different tissues in a tumor from the lung cancer/breast cancer H&E stained graphs, and generate the final segmentation result, so as to intuitively display spatial distribution of an internal tissue structure of the tumor and help doctors to grade lung cancer/breast cancer patients and analyze prognosis.

The above-mentioned embodiment is only a description of a preferred mode of the disclosure, and does not limit a scope of the disclosure. Under a premise of not departing from a design spirit of the disclosure, various modifications and improvements made by ordinary technicians in a field to a technical scheme of the disclosure shall fall within the scope of protection determined by claims of the disclosure.

What is claimed is:

1. A weakly supervised pathological image tissue segmentation method based on an online noise suppression strategy, comprising:

acquiring an H&E stained graph, processing the H&E stained graph to obtain a data set, dividing the data set, training a classification network based on a divided data set, and generating a pseudo-label;

suppressing a noise existing in the pseudo-label based on the online noise suppression strategy, and training a semantic segmentation network through the pseudo-label after noise suppression and a training set corresponding to the pseudo-label to obtain a prediction result of the semantic segmentation network after the training, and taking the prediction result as a final segmentation result;

acquiring the H&E stained graph comprises:

collecting pathological section images of cancerous tissues of lung cancer/breast cancer patients, dyeing the pathological section images to obtain H&E stained pathological sections of lung cancer/breast cancer, and then digitizing the H&E stained pathological sections of the lung cancer/breast cancer to obtain the H&E stained graph;

processing the H&E stained graph comprises:

delineating a region of interest of the H&E stained graph, cutting the region of interest into sub-image blocks of a same series without overlapping, adding a patch-level label to each of the sub-image blocks, and specifying a tissue category existing in the patch-level label;

dividing the data set, training the classification network based on the divided data set, and generating the pseudo-label comprise:

dividing the training set, a verification set and a test set according to the data set, constructing the classification network by using a deep learning model, carrying out data enhancement processing on the training set, training the classification network based on the training set after the data enhancement processing, internally verifying classification performance of the classification network through the verification set, and externally verifying the classification performance of the classification network through the test set to obtain a trained classification network, and using Grad-CAM++ to generate the pseudo-label based on the trained classification network.

2. The weakly supervised pathological image tissue segmentation method based on the online noise suppression strategy according to claim 1, wherein training the classification network based on the training set after the data enhancement processing comprises:

pre-training the classification network based on a large public image database to obtain an initial model of the classification network, setting a training scheme and hyper parameters of the initial model of the classification network, training the initial model of the classification network based on the training set after the data enhancement processing, introducing a progressive attention-discarding mechanism, and iteratively erasing most discriminating regions, forcing the initial model of the classification network to learn non-discriminating regions;

wherein a weight of each layer of the initial model of the classification network is set to an updatable mode.

3. The weakly supervised pathological image tissue segmentation method based on the online noise suppression strategy according to claim 1, wherein suppressing the noise existing in the pseudo-label based on the online noise suppression strategy comprises:

calculating the pseudo-label and prediction confidence pixel by pixel based on standard cross entropy to obtain a loss map, selecting a loss of the loss map by improving a weighted cross entropy loss, and giving different weights to different pixel points according to the loss of the loss map to suppress the noise existing in the pseudo-label.

4. The weakly supervised pathological image tissue segmentation method based on the online noise suppression strategy according to claim 3, wherein a method for improving the weighted cross entropy loss comprises is:

$$\mathcal{L}_{seg} = -\sum_{j=0}^{w}\sum_{i=0}^{h} W_{i,j} \cdot \log \frac{\exp(P_{\mathcal{M}_{i,j},i,j})}{\sum_{c=1}^{C}(\exp(P_{c,i,j}))}$$

wherein $\mathcal{L}_{seg}$ is a loss of a segmentation network, W∈ $\mathbb{R}^{H+W}$ is a loss weight, H and W respectively represent dimensions, and i and j respectively represent coordinates, P is prediction of the segmentation network, $\mathcal{M}$ is the pseudo-label, $$\sum_{c=1}^{C}(\exp(P_{c,i,j}))$$

is, and C is a category.

5. The weakly supervised pathological image tissue segmentation method based on the online noise suppression strategy according to claim 3, wherein a method of giving different weights to the different pixel points is:

$$W = \frac{sm(-\mathcal{L})}{\text{mean}(sm(-\mathcal{L}))}$$

wherein $sm(-\mathcal{L})$ is to assign a high loss value to a low value, sm is to use a softmax function in HW dimensions, and $\text{mean}(sm(-\mathcal{L}))$ is an average value of assigning the high loss value to the low value, sm is the softmax function, and a loss in $\mathcal{L} \in \mathbb{R}^{H+W}$ is used as an index indicating a degree of learning difficulty, and W is a weight.

6. The weakly supervised pathological image tissue segmentation method based on the online noise suppression strategy according to claim 1, wherein training the semantic segmentation network through the pseudo-label after the noise suppression and the training set corresponding to the pseudo-label comprises:

carrying out the data enhancement processing on the training set corresponding to the pseudo-label, setting the training scheme and the hyper parameters of the classification network, and training the semantic segmentation network through the pseudo-label after the noise suppression and the training set after the data enhancement processing.

7. The weakly supervised pathological image tissue segmentation method based on the online noise suppression strategy according to claim 1, wherein taking the prediction result of the semantic segmentation network after the training as the final segmentation result comprises:

using an overlapping sliding window prediction operation under a preset magnification of the H&E stained graph, intercepting image blocks with a same pixel size, and obtaining a overlapping rate of the image blocks, sending the image blocks into the semantic segmentation network after the training to obtain probability maps of several channels, stitching the probability maps into a WSI level, calculating an average value of each category prediction probability of each pixel position for overlapping regions, and acquiring a WSI segmentation result through an argmax operation;

segmenting the probability maps stitched as the WSI level by a threshold segmentation method when a background region is segmented, and setting points with gray scale pixel values greater than a preset value as fixed values to obtain a gray scale map; and adding the gray scale map to the WSI segmentation result to obtain the final segmentation result.

\* \* \* \* \*